US007888457B2

(12) United States Patent
Allen et al.

(10) Patent No.: US 7,888,457 B2
(45) Date of Patent: Feb. 15, 2011

(54) PROCESS FOR REMOVING PHOSPHOROUS FROM A FIBER OR YARN

(75) Inventors: Steven R Allen, Midlothian, VA (US); Doetze Jakob Sikkema, Richmond, VA (US)

(73) Assignees: E. I. du Pont de Nemours and Company, Wilmington, DE (US); Magellan Systems International, LLC, Bethesda, MD (US)

( * ) Notice: Subject to any disclaimer, the term of this patent is extended or adjusted under 35 U.S.C. 154(b) by 672 days.

(21) Appl. No.: 11/909,670

(22) PCT Filed: Mar. 27, 2006

(86) PCT No.: PCT/US2006/011513

§ 371 (c)(1),
(2), (4) Date: Sep. 25, 2007

(87) PCT Pub. No.: WO2006/105225

PCT Pub. Date: Oct. 5, 2006

(65) Prior Publication Data

US 2010/0184944 A1  Jul. 22, 2010

Related U.S. Application Data

(60) Provisional application No. 60/665,741, filed on Mar. 28, 2005.

(51) Int. Cl.
C08F 6/00 (2006.01)
C08J 3/00 (2006.01)

(52) U.S. Cl. .................. 528/486; 428/364; 502/150; 502/208; 528/503

(58) Field of Classification Search ............. 428/364; 502/150, 208; 528/486, 503
See application file for complete search history.

(56) References Cited

U.S. PATENT DOCUMENTS

| | | | |
|---|---|---|---|
| 3,227,793 A | 1/1966 | Cipiani | 264/203 |
| 3,414,645 A | 12/1968 | Morgan, Jr. | 264/210 |
| 3,424,720 A | 1/1969 | Rudner et al. | 260/47 |
| 3,767,756 A | 10/1973 | Blades | 264/184 |
| 3,804,804 A | 4/1974 | Gerber et al. | 260/47 CP |
| 3,940,955 A | 3/1976 | Welsh | 68/20 |
| 3,996,979 A | 12/1976 | Weinberger | 264/40.3 |
| 4,002,679 A | 1/1977 | Arnold | 260/556 A |
| 4,070,431 A | 1/1978 | Lewis et al. | 264/180 |
| 4,078,034 A | 3/1978 | Lewis | 264/181 |
| 4,079,039 A | 3/1978 | Gerber | 260/47 CP |
| 4,298,565 A | 11/1981 | Yang | 264/181 |
| 4,452,971 A | 6/1984 | Choe et al. | 528/336 |
| 4,533,693 A | 8/1985 | Wolfe et al. | 524/417 |
| 4,703,103 A | 10/1987 | Wolfe et al. | 528/179 |
| 4,772,678 A | 9/1988 | Sybert et al. | 528/179 |
| 4,845,150 A | 7/1989 | Kovak et al. | 524/602 |
| 4,847,350 A | 7/1989 | Harris | 528/179 |
| 4,898,924 A | 2/1990 | Chenevey et al. | 528/183 |
| 4,939,235 A | 7/1990 | Harvey et al. | 528/337 |
| 4,963,428 A | 10/1990 | Harvey et al. | 428/220 |
| 5,041,522 A | 8/1991 | Dang et al. | 528/183 |
| 5,089,591 A | 2/1992 | Gregory et al. | 528/185 |
| 5,168,011 A | 12/1992 | Kovar et al. | 428/373 |
| 5,276,128 A | 1/1994 | Rosenberg et al. | 528/184 |
| 5,367,042 A | 11/1994 | Pierini et al. | 528/183 |
| 5,393,478 A * | 2/1995 | Sen et al. | 264/203 |
| 5,429,787 A | 7/1995 | Im et al. | 264/344 |
| 5,525,638 A * | 6/1996 | Sen et al. | 521/61 |
| 5,552,221 A | 9/1996 | So et al. | 428/373 |
| 5,667,743 A | 9/1997 | Tai et al. | 264/184 |
| 5,674,969 A * | 10/1997 | Sikkema et al. | 528/183 |
| 5,772,942 A * | 6/1998 | Teramoto et al. | 264/184 |
| 6,228,922 B1 | 5/2001 | Wang et al. | 542/413 |
| 7,683,157 B2 * | 3/2010 | Allen et al. | 528/423 |
| 2003/0083421 A1 | 5/2003 | Kumar et al. | 524/496 |
| 2006/0019094 A1 | 1/2006 | Lee | 428/364 |
| 2006/0287475 A1 * | 12/2006 | Allen et al. | 528/272 |
| 2008/0179776 A1 * | 7/2008 | Allen et al. | 264/103 |
| 2008/0287647 A1 * | 11/2008 | Sikkema | 528/396 |

FOREIGN PATENT DOCUMENTS

| | | |
|---|---|---|
| EP | 0 481 403 B1 | 5/1996 |
| EP | 0 834 608 B1 | 3/2002 |
| EP | 834608 * | 4/2004 |
| EP | 1 553 143 A1 | 7/2005 |
| GB | 1 361 840 | 7/1974 |
| JP | 06-240596 | 8/1994 |
| JP | 09-78349 | 3/1997 |
| WO | WO 91/02764 A1 | 3/1991 |
| WO | WO 94/12702 A1 | 6/1994 |

(Continued)

OTHER PUBLICATIONS

Gerber, A.H., "Thermally stable polymers derived from 2,3,5,6-tetraaminopyridine," J. of Polymer Science, 1973, 11, 1703-1719.

(Continued)

Primary Examiner—Terressa M Boykin
(74) Attorney, Agent, or Firm—Woodcock Washburn LLP

(57) ABSTRACT

The present invention relates to processes for removing phosphorus from a fiber or yarn.

19 Claims, 1 Drawing Sheet

FOREIGN PATENT DOCUMENTS

| | | | |
|---|---|---|---|
| WO | WO 9610661 | * | 4/1996 |
| WO | WO 96/20303 A1 | | 7/1996 |
| WO | WO 99/27169 A1 | | 6/1999 |
| WO | WO2004/003080 A1 | | 1/2004 |
| WO | WO 2004/003269 A1 | | 1/2004 |
| WO | WO 2004003080 | * | 1/2004 |
| WO | WO 2004/024797 A1 | | 2/2004 |
| WO | WO 2004024797 | * | 3/2004 |
| WO | WO 2006/014718 A1 | | 2/2006 |
| WO | WO 2006/105076 A2 | | 10/2006 |
| WO | WO 2006/105225 A1 | | 10/2006 |
| WO | WO 2006/105226 A1 | | 10/2006 |
| WO | WO 2006/105231 A1 | | 10/2006 |

OTHER PUBLICATIONS

Lammers, M., et al., "Mechanical properties and structural transitions in the new rigid-rod polymer fibre PIPD ('M5') during the manufacturing process," Elsevier Sci. Ltd., 1997, S0032-3861, 7 pages.

Sikkema, D.J., "Design, synthesis and properties of a novel rigid rod polymer, PIPD or 'M5': high modulus and tenacity fibers with substantial compressive strength," Polymer, 1998, 39(24), 5981-5986.

* cited by examiner

PROCESS FOR REMOVING PHOSPHOROUS FROM A FIBER OR YARN

CROSS-REFERENCE TO RELATED APPLICATIONS

This application is the National Stage of International Application No. PCT/US2006/011513, filed Mar. 27, 2006, which claims the benefit of U.S. Provisional Application Nos. 60/665,741, filed Mar. 28, 2005, the disclosure of which is incorporated herein by reference in it's entirety.

FIELD OF THE INVENTION

The present invention generally relates to polymer fibers and processes for the preparation of such fibers. More particularly, the present invention relates to methods of removing polyphosphoric acid, inter alia, from filaments and spun yarns comprising polymers.

BACKGROUND OF THE INVENTION

Many fibers are prepared from a solution of the polymer in a solvent (called the "polymer dope") by extruding or spinning the polymer dope through a die or spinneret to prepare or spin a dope filament. The solvent is subsequently removed to provide the fiber or yarn. In the preparation of certain fibers, the solvent utilized is a solvent acid, such as polyphosphoric acid (PPA). Unlike many typical solvents, PPA removal is generally more difficult, in part due to its polymeric nature. Incorporation of heteroatoms into the polymer may also act to inhibit removal of polyphosphoric acid from the fiber or yarn. Existing processes for removal of polymeric PPA solvent from a polymeric material typically require long washing times or elevated leaching temperatures if a substantial amount of PPA is to be removed.

For example, Sen et al., U.S. Pat. No. 5,393,478, discloses a process for leaching polyphosphoric acid from the polybenzazole dope filament by contacting with a leaching fluid at a temperature of at least about 60° C.

Sen et al., U.S. Pat. No. 5,525,638, discloses a process for washing polyphosphoric acid from the polybenzazole dope filament by using multiple washes, typically at about room temperature, slowly reducing phosphorous concentration from the spun fiber, allegedly to improve the physical properties of the resultant polymeric fiber.

Further improvements in the physical properties of and/or removal of phosphorous from fibers spun from polyphosphoric acid are needed. These and other objects of the invention will become more apparent from the present specification and claims.

SUMMARY OF THE INVENTION

The present invention is directed, in part, to processes for removing polyphosphoric acid from a fiber, comprising the steps of heating a fiber comprising polymer and polyphosphoric acid to at least 120 degrees Celsius ("° C.") for a time effective to hydrolyze polyphosphoric acid; and in a separate step, removing hydrolyzed polyphosphoric acid from the fiber with a fluid having a temperature of 100° C. or less.

The present invention is also directed, in part, to processes for hydrolyzing polyphosphoric acid in a fiber, comprising the step of heating a fiber comprising polymer and polyphosphoric acid in an acidic medium having a pH less than 4.0 to a temperature above 100° C. for a time effective to hydrolyze polyphosphoric acid.

The invention is also directed, in part, to processes for hydrolyzing polyphosphoric acid in a polyareneazole polymeric material, comprising the steps of providing a polymeric material comprising polyareneazole and polyphosphoric acid, wherein at least 50 mole percent of the polyareneazole repeating unit structures comprise 2,5-dihydroxy-p-phenylene moieties; and heating the polymeric material to more than 100° C. to hydrolyze at least a portion of polyphosphoric acid.

The invention is further directed, in part, to processes for removing phosphorus from a yarn spun from a polymer solution containing polyphosphoric acid, the yarn comprising at least about 1.5 percent by weight of the yarn of phosphorous, comprising contacting the yarn with a base and washing the yarn with an aqueous fluid.

The invention also provides fibers comprising polyareneazole polymer having pendant hydroxyl groups and at least 2 percent based on fiber weight of cations including sodium, potassium, or calcium, or any combination thereof.

The present invention is also directed, in part, to processes for removing cations from a polyareneazole fiber, comprising the steps of providing a fiber comprising a polyareneazole polymer having pendant hydroxyl groups and at least 2 percent by weight of cations, contacting the fiber with an aqueous solution containing acid to release at least a portion of the cations, and, optionally, washing the fiber with water.

BRIEF DESCRIPTION OF THE DRAWINGS

The invention may be more fully understood from the following detailed description thereof in connection with accompanying drawings described as follows.

DETAILED DESCRIPTION OF ILLUSTRATIVE EMBODIMENTS

Figure 1:
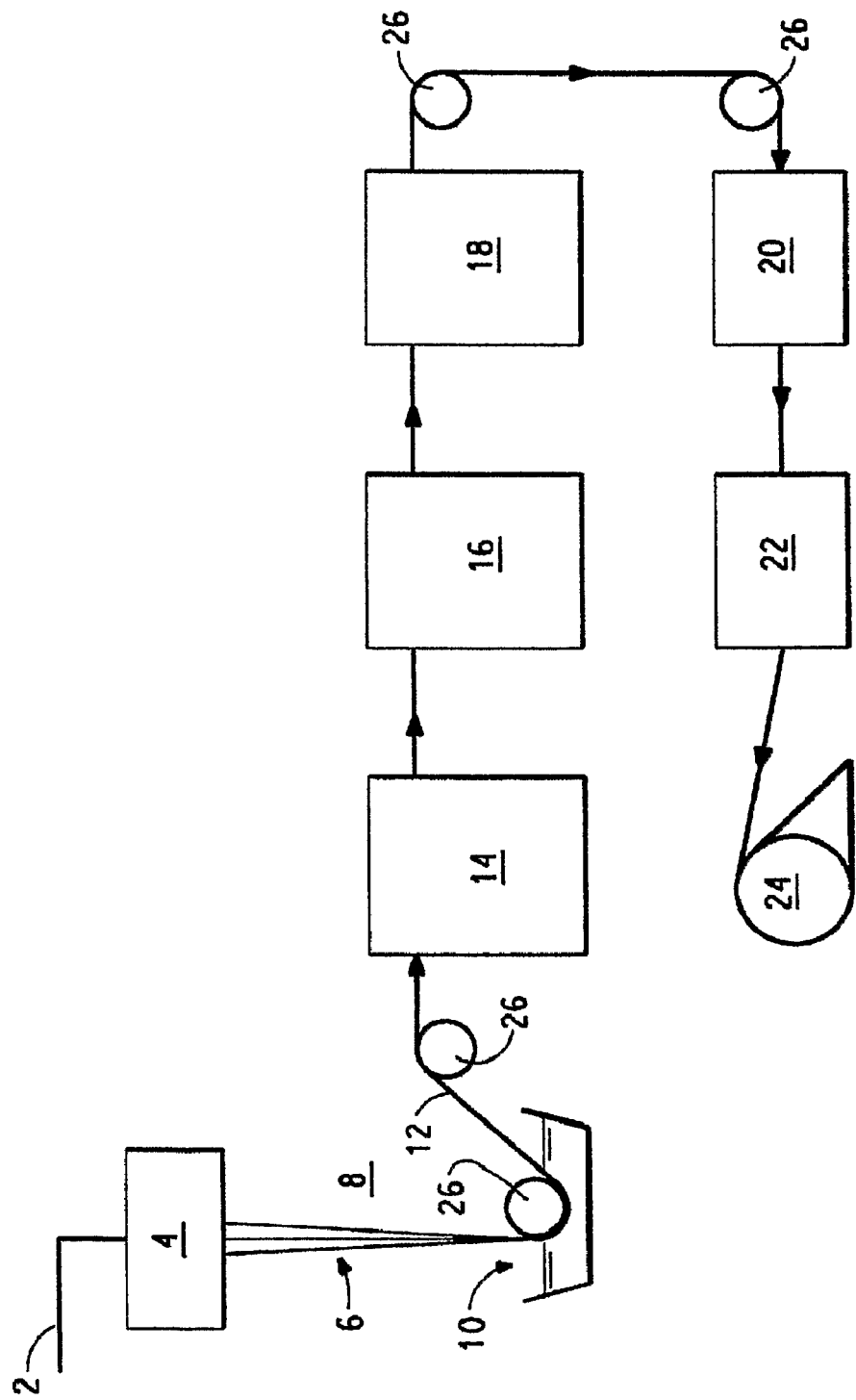
FIG. 1 is a schematic diagram of a polyarenezole fiber production process.

As employed above and throughout the disclosure, the following terms, unless otherwise indicated, shall be understood to have the following meanings.

Filaments of the present invention can be made from polyareneazole polymer. As defined herein, "polyareneazole" refers to polymers having either:

one hetero aromatic ring fused with an adjacent aromatic group (Ar) of repeating unit structure (a):

(a)

wherein N is a nitrogen atom and Z is a sulfur, oxygen, or NR group wherein R is hydrogen or a substituted or unsubstituted alkyl or aryl attached to N; or two hetero aromatic rings each fused to a common aromatic group (Ar¹) of either of the repeating unit structures (b1 or b2):

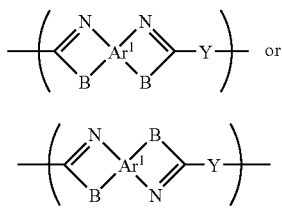

(b1)

(b2)

wherein N is a nitrogen atom and B is an oxygen, sulfur, or NR group, wherein R is hydrogen or a substituted or unsubstituted alkyl or aryl attached to N. The number of repeating unit structures represented by structures (a), (b1), and (b2) is not critical. Preferably, each polymer chain has from 10 to 25,000 repeating units. Polyareneazole polymers include polybenzazole polymers or polypyridazole polymers or both. In certain embodiments, the polybenzazole polymers comprise polybenzimidazole or polybenzobisimidazole polymers. In certain other embodiments, the polypyridazole polymers comprise polypyridobisimidazole or polypyridoimidazole polymers. In certain preferred embodiments, the polymers are of a polybenzobisimidazole or polypyridobisimidazole type.

In structure (b1) and (b2), Y is an aromatic, heteroaromatic, aliphatic group, or nil; preferably an aromatic group; more preferably a six-membered aromatic group of carbon atoms. Still more preferably, the six-membered aromatic group of carbon atoms (Y) has para-oriented linkages with two substituted hydroxyl groups; even more preferably 2,5-dihydroxy-para-phenylene.

In structures (a), (b1), or (b2), Ar and $Ar^1$ each represent any aromatic or heteroaromatic group. The aromatic or heteroaromatic group can be a fused or non-fused polycyclic system, but is preferably a single six-membered ring. More preferably, the Ar or $Ar^1$ group is preferably heteroaromatic, wherein a nitrogen atom is substituted for one of the carbon atoms of the ring system or Ar or $Ar^1$ may contain only carbon ring atoms. Still more preferably, the Ar or $Ar^1$ group is heteroaromatic.

As herein defined, "polybenzazole" refers to polyareneazole polymer having repeating structure (a), (b1), or (b2) wherein the Ar or $Ar^1$ group is a single six-membered aromatic ring of carbon atoms. Preferably, polybenzazoles are a class of rigid rod polybenzazoles having the structure (b1) or (b2); more preferably rigid rod polybenzazoles having the structure (b1) or (b2) with a six-membered carbocyclic aromatic ring $Ar^1$. Such preferred polybenzazoles include, but are not limited to polybenzimidazoles (B=NR polybenzthiazoles (B=S), polybenzoxazoles (B=O), and mixtures or copolymers thereof. When the polybenzazole is a polybenzimidazole, preferably it is poly(benzo[1,2-d:4,5-d']bisimidazole-2,6-diyl-1,4-phenylene. When the polybenzazole is a polybenzthiazole, preferably it is poly(benzo[1,2-d:4,5-d']bisthiazole-2,6-diyl-1,4-phenylene. When the polybenzazole is a polybenzoxazole, preferably it is poly(benzo[1,2-d:4,5-d']bisoxazole-2,6-diyl-1,4-phenylene.

As herein defined, "polypyridazole" refers to polyareneazole polymer having repeating structure (a), (b1), or (b2) wherein the Ar or $Ar^1$ group is a single six-membered aromatic ring of five carbon atoms and one nitrogen atom. Preferably, these polypyridazoles are a class of rigid rod polypyridazoles having the structure (b1) or (b2), more preferably rigid rod polypyridazoles having the structure (b1) or (b2) with a six-membered heterocyclic aromatic ring $Ar^1$. Such more preferred polypyridazoles include, but are not limited to polypyridobisimidazole (B=NR), polypyridobisthiazole (B=S), polypyridobisoxazole (B=O), and mixtures or copolymers thereof. Yet more preferred, the polypyridazole is a polypyridobisimidazole (B=NR) of structure:

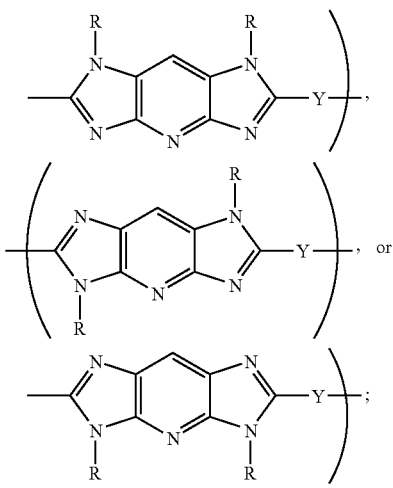

wherein N is a nitrogen atom, R is hydrogen or a substituted or unsubstituted alkyl or aryl attached to N, preferably wherein R is H, and Y is as previously defined. The number of repeating structures or units represented by structures is not critical. Preferably, each polymer chain has from 10 to 25,000 repeating units.

Filaments of the present invention are prepared from polybenzazole (PBZ) or polypyridazole polymers. For purposes herein, the term "filament" or "fiber" refers to a relatively flexible, macroscopically homogeneous body having a high ratio of length to width across its cross-sectional area perpendicular to its length. The filament cross section may be any shape, but is typically circular.

As herein defined, "yarn" refers to a number of filaments laid, bundled, or assembled together with or without a degree of twist or interlacing, forming a continuous strand, which can be used, for example, in weaving, knitting, plaiting, or braiding, wherein fiber is as defined hereinabove.

For purposes herein, "fabric" refers to any woven, knitted, or non-woven structure. By "woven" is meant any fabric weave, such as, plain weave, crowfoot weave, basket weave, satin weave, twill weave, and the like. By "knitted" is meant a structure produced by interlooping or intermeshing one or more ends, fibers or multifilament yarns. By "non-woven" is meant a network of fibers, including unidirectional fibers, felt, and the like.

As herein defined, "coagulation bath" refers to a medium provided to coagulate the dope filament. The bath comprises a liquid, typically an alcohol, water, aqueous acid, or other aqueous liquid mixture. Preferably, the bath is water or aqueous phosphoric acid, but the liquid may be anything that provides water or other moiety that may assist in the hydrolysis of PPA.

In some embodiments, the more preferred rigid rod polypyridazoles include, but are not limited to polypyridobisimidazole homopolymers and copolymers such as those described in U.S. Pat. No. 5,674,969 (to Sikkema, et al. on Oct. 7, 1997). One such exemplary polypyridobisimidazole is homopolymer poly(1,4-(2,5-dihydroxy)phenylene-2,6-diimidazo[4,5-b:4'5'-e]pyridinylene).

The polyareneazole polymers used in this invention may have properties associated with a rigid-rod structure, a semi-rigid-rod structure, or a flexible coil structure; preferably a rigid rod structure. When this class of rigid rod polymers has structure (b1) or (b2) it preferably has two azole groups fused to the aromatic group $Ar^1$.

Suitable polyareneazoles useful in this invention include homopolymers and copolymers. Up to as much as 25 percent, by weight, of other polymeric material can be blended with the polyareneazole. Also copolymers may be used having as much as 25 percent or more of other polyareneazole monomers or other monomers substituted for a monomer of the majority polyareneazole. Suitable polyareneazole homopolymers and copolymers can be made by known procedures, such as those described in U.S. Pat. No. 4,533,693 (to Wolfe et al. on Aug. 6, 1985), U.S. Pat. No. 4,703,103 (to Wolfe et al. on Oct. 27, 1987), U.S. Pat. No. 5,089,591 (to Gregory et al. on Feb. 18, 1992), U.S. Pat. No. 4,772,678 (Sybert et al. on Sep. 20, 1988), U.S. Pat. No. 4,847,350 (to Harris et al. on Aug. 11, 1992), U.S. Pat. No. 5,276,128 (to Rosenberg et al. on Jan. 4, 1994) and U.S. Pat. No. 5,674,969 (to Sikkema, et al. on Oct. 7, 1997). Additives may also be incorporated in the polyareneazole in desired amounts, such as, for example, anti-oxidants, lubricants, ultra-violet screening agents, colorants and the like.

This invention is generally directed to polyareneazole filaments, more specifically to polybenzazole (PBZ) filaments or polypyridazole filaments, and processes for the preparation of such filaments. The invention further relates to yarns, fabrics, and articles incorporating filaments of this invention, and processes for making such yarns, fabrics, and articles.

When any variable occurs more than one time in any constituent or in any formula, its definition in each occurrence is independent of its definition at every other occurrence. Combinations of substituents and/or variables are permissible only if such combinations result in stable compounds.

Accordingly, in certain embodiments, the present invention is directed to processes for removing polyphosphoric acid from a fiber, comprising the steps of heating a fiber comprising polymer and polyphosphoric acid typically to at least 120° C. for a time effective to hydrolyze polyphosphoric acid; and in a separate step, removing hydrolyzed polyphosphoric acid from the fiber with a fluid having a temperature of 100° C. or less. In some embodiments, the time effective to hydrolyze polyphosphoric acid is up to about 120 seconds. In other embodiments, the step of heating a fiber may include convective heating, radiant heating, radiation heating, RF heating, conductive heating, steam heating, or any combination thereof. In still other embodiments, the polymer comprises a polyareneazole; more preferably wherein the polyareneazole is a polypyridazole. In certain other embodiments, the polyareneazole is a polypyridobisimidazole; more preferably poly(1,4-(2,5-dihydroxy)phenylene-2,6-diimidazo[4,5-b:4'5'-e]pyridinylene). In still other embodiments, the polyareneazole is a polybenzazole, and more preferably a polybenzobisoxazole. More typically in some embodiments, removing hydrolyzed polyphosphoric acid includes washing the fiber with a base; more preferably, the fiber is washed with water prior to and after washing with the base. Typically, the base must be selected to be strong enough to break a bond between the polymer and the phosphoric acid and typically includes sodium hydroxide, potassium hydroxide, ammonium hydroxide, sodium bicarbonate, or any combination thereof, preferably sodium hydroxide, potassium hydroxide, or any combination thereof. In certain embodiments, removing hydrolyzed polyphosphoric acid includes washing the fiber with a base and subsequent washing with acid. In other embodiments, the steps of cooling the fiber to less than 60° C. and removing hydrolyzed polyphosphoric acid from the fiber occur simultaneously. In still other embodiments, the fluid used to remove hydrolyzed polyphosphoric acid has a temperature of about 60° C. or less.

In various embodiments of the processes of the present invention for hydrolyzing polyphosphoric acid in a fiber, fiber comprising polymer and polyphosphoric acid is typically heated in an acidic medium having a pH less than 4.0 to a temperature above 100° C. for a time effective to hydrolyze polyphosphoric acid. In some embodiments, the time effective to hydrolyze polyphosphoric acid is up to about 120 seconds. In some other embodiments, the acidic medium comprises up to about 80% phosphoric acid by weight. In certain embodiments the acidic medium more typically has a pH less than 3.0, and preferably less than 2.0. In certain embodiments, the acidic medium preferably comprises boiling phosphoric acid having a temperature less than 140° C. Although hydrolyzed polyphosphoric acid need not be removed from the fiber, in certain embodiments the process further comprises the step of removing hydrolyzed polyphosphoric acid from the fiber. In a preferred embodiment, the polymer remains substantially non-hydrolyzed after hydrolyzing the polyphosphoric acid. As herein defined, when the polymer "remains substantially non-hydrolyzed", it is meant that the polymer inherent viscosity is not materially affected by the process.

In other embodiments, the present invention is directed to processes for hydrolyzing polyphosphoric acid in a polyareneazole polymeric material, comprising the steps of a) providing a polymeric material comprising polyareneazole and polyphosphoric acid, wherein at least 50 mole percent of the polyareneazole repeating unit structures comprise 2,5-dihydroxy-para-phenylene moieties; and b) typically heating the polymeric material to more than 100° C. to hydrolyze at least a portion of polyphosphoric acid. More typically, the process further comprises the step of removing hydrolyzed polyphosphoric acid from the polymeric material.

In other embodiments, the invention is directed to processes for removing phosphorus from a yarn spun from a polymer solution containing polyphosphoric acid, the yarn comprising at least about 1.5 percent by weight of the yarn of phosphorus, comprising typically contacting the yarn with a base and washing the yarn with an aqueous fluid. In certain embodiments, the phosphorus content of the yarn prior to contacting the yarn with the base is typically in the range of from 2 to 20 percent based on yarn weight, more typically the phosphorus content is in the range of 4 to 15 percent based on yarn weight. In some embodiments, contacting the yarn with the base includes spraying, coating, flowing, drawing, dipping, or any combination thereof. Typically, the base contacting the yarn includes sodium hydroxide, potassium hydroxide, ammonium hydroxide, sodium bicarbonate, or any combination thereof. In other embodiments, the aqueous fluid typically used in washing the yarn contains an acid, more typically a volatile acid. Suitable, non-limiting examples of volatile acids include formic acid, acetic acid, propionic acid, butyric acid, isobutyric acid, pivalic acid, or any combination thereof. Preferably, the volatile acid is acetic or propionic acid. In certain embodiments, the polymer comprises a polyareneazole. Preferably, the polyareneazole is a polypyridazole; more preferably a polypyridobisimidazole. Even more preferred in some embodiments, the polyareneazole is poly(1,4-(2,5-dihydroxy)phenylene-2,6-diimidazo[4,5-b:4'5'-e]pyridinylene). In other embodiments, the polyareneazole is a polybenzazole, more typically a polybenzobisoxazole.

In still other processes for removing phosphorus from a yarn spun from a polymer solution containing polyphosphoric acid, the yarn typically contains ≦0.1 percent phosphorus based on yarn weight after washing with the aqueous fluid. The yarn is provided, in certain embodiments, by heating a spun multifilament yarn comprising the polymer and polyphosphoric acid to at least 120° C. for a time effective to hydrolyze polyphosphoric acid, preferably up to about 600 seconds, more preferably up to about 120 seconds. In certain embodiments, the base used in contacting the yarn is aqueous sodium hydroxide, or the aqueous washing fluid contains acetic acid, or both. In other embodiments, the duration of the contacting step with base is typically no more than 30 seconds, preferably 20 seconds or less. Similarly, in certain other embodiments, the duration of the washing step with aqueous fluid is no more than 30 seconds, preferably 20 seconds or less. In still other embodiments, the step of contacting the yarn with a base begins before the step of washing the yarn with an aqueous fluid.

In certain embodiments, the invention is directed to fibers comprising polyareneazole polymer having pendant hydroxyl groups and at least 2 percent based on fiber weight of cations including sodium, potassium, or calcium, or any combination thereof. In some embodiments, the polyareneazole is typically a polypyridazole, preferably a polypyridobisimidazole. Even more preferred, the polypyridobisimidazole is poly(1,4-(2,5-dihydroxy)phenylene-2,6-diimidazo[4,5-b:4'5'-e]pyridinylene). In other embodiments, the polyareneazole is a polybenzazole, typically a polybenzobisoxazole. In certain embodiments, the fiber typically contains greater than 2 percent based on fiber weight of sodium. In still other embodiments, the fiber contains typically greater than 3 percent based on fiber weight of the cations. In certain embodiments, the fiber contains greater than 3 percent based on fiber weight of sodium.

In other embodiments, the invention is directed to a process for removing cations from a polyareneazole fiber, comprising the steps of a) providing a fiber comprising a polyareneazole polymer having pendant hydroxyl groups, and at least 2 percent by weight of cations, b) contacting the fiber with an aqueous solution containing acid to release at least a portion of the cations, and c) optionally, washing the fiber with water. In certain embodiments, the acid is more typically a volatile acid. Suitable, non-limiting examples of volatile acids include formic acid, acetic acid, propionic acid, butyric acid, isobutyric acid, pivalic acid, or any combination thereof; preferably acetic acid, propionic acid, or any combination thereof. In some embodiments, the aqueous solution typically contains from about 0.1 to about 10 percent by weight acid. In other embodiments, the cations being removed from polyareneazole fibers include sodium, potassium, calcium, or any combination thereof. Contacting the fiber with the aqueous solution typically includes spraying, coating, flowing, drawing, dipping, or any combination thereof. While the contacting step may be shorter or longer depending on the specific polymer or fiber, typically the duration of the contacting step is up to about 30 seconds, preferably up to about 20 seconds or less. Likewise the optional washing step time may not be critical, but typically the duration of the optional washing step is up to about 30 seconds, preferably up to about 20 seconds or less. In certain embodiments, the fiber contains up to about 0.1 percent cations based on fiber weight after the steps of contacting the fiber with an aqueous solution containing acid, and optionally washing the fiber with water, preferably up to about 0.05 percent cations based on fiber weight. In other embodiments, the fiber further comprises at least about 0.1 percent phosphorus based on fiber weight prior to contacting the fiber with the aqueous solution, more typically at least about 1 percent phosphorus based on fiber weight prior to contacting the fiber with the aqueous solution. In still other embodiments, the polyareneazole is a polypyridazole, typically a polypyridobisimidazole. In certain preferred embodiments, the polypyridobisimidazole is poly(1,4-(2,5-dihydroxy)phenylene-2,6-diimidazo[4,5-b:4'5'-e]pyridinylene). In yet other embodiments, the polyareneazole is a polybenzazole, preferably a polybenzobisoxazole.

Suitable polyareneazole monomers are reacted in a solution of non-oxidizing and dehydrating acid under non-oxidizing atmosphere with mixing at a temperature that is increased in step-wise or ramped fashion from no more than about 120° C. to at least about 170° C. The polyareneazole polymer can be rigid rod, semi-rigid rod or flexible coil. It is preferably a lyotropic liquid-crystalline polymer, which forms liquid-crystalline domains in solution when its concentration exceeds a critical concentration. The inherent viscosity of rigid polyareneazole polymers in methanesulfonic acid at 30° C., is preferably at least about 10 dL/g, more preferably at least about 15 dL/g and most preferably at least about 20 dL/g.

Certain embodiments of the present invention are discussed in reference to FIG. 1. In some embodiments, the polymer is formed in acid solvent providing the dope solution 2. In other embodiments, the polymer is dissolved in the acid solvent after formation. Either is within the ambit of the invention. Preferably the polymer is formed in acid solvent and provided for use in the invention. The dope solution 2, comprising polymer and polyphosphoric acid, typically contains a high enough concentration of polymer for the polymer to form an acceptable filament 6 after extrusion and coagulation. When the polymer is lyotropic liquid-crystalline, the concentration of polymer in the dope 2 is preferably high enough to provide a liquid-crystalline dope. The concentration of the polymer is preferably at least about 7 weight percent, more preferably at least about 10 weight percent and most preferably at least about 14 weight percent. The maximum concentration is typically selected primarily by practical factors, such as polymer solubility and dope viscosity. The concentration of polymer is preferably no more than 30 weight percent, and more preferably no more than about 20 weight percent.

The polymer dope solution 2 may contain additives such as anti-oxidants, lubricants, ultra-violet screening agents, colorants and the like which are commonly incorporated.

The polymer dope solution 2 is typically extruded or spun through a die or spinneret 4 to prepare or spin the dope filament. The spinneret 4 preferably contains a plurality of holes. The number of holes in the spinneret and their arrangement is not critical to the invention, but it is desirable to maximize the number of holes for economic reasons. The spinneret 4 can contain as many as 100 or 1000 or more holes, and they may be arranged in circles, grids, or in any other desired arrangement. The spinneret 4 may be constructed out of any materials that will not be degraded by the dope solution 2.

Fibers may be spun from solution using any number of processes, however, wet spinning and "air-gap" spinning are the best known. The general arrangement of the spinnerets and baths for these spinning processes is well known in the art, with the figures in U.S. Pat. Nos. 3,227,793; 3,414,645; 3,767,756, and 5,667,743 being illustrative of such spinning processes for high strength polymers. In "air-gap" spinning the spinneret typically extrudes the fiber first into a gas, such as air. Using FIG. 1 to help illustrate a process employing "air-gap" spinning (also sometimes known as "dry-jet" wet spinning), dope solution 2 exiting the spinneret 4 enters a gap 8 (typically called an "air gap" although it need not contain air) between the spinneret 4 and a coagulation bath 10 for a very short duration of time. The gap 8 may contain any fluid that does not induce coagulation or react adversely with the dope, such as air, nitrogen, argon, helium, or carbon dioxide. The extruded dope 6 is drawn across the air gap 8, with or without stretching and immediately introduced into a liquid coagulation bath. Alternately, the fiber may be "wet-spun". In wet spinning, the spinneret typically extrudes the fiber directly into the liquid of a coagulation bath and normally the spinneret is immersed or positioned beneath the surface of the coagulation bath. Either spinning process may be used to provide fibers for use in the processes of the invention. In some embodiments of the present invention, air-gap spinning is preferred.

The extruded dope 6 is "coagulated" in the coagulation bath 10 containing water or a mixture of water and phosphoric acid, which removes enough of the polyphosphoric acid to prevent substantial stretching of the extruded dope 6 during any subsequent processing. If multiple fibers are extruded simultaneously, they may be combined into a multifilament yarn before, during or after the coagulation step. The term "coagulation" as used herein does not necessarily imply that the extruded dope 6 is a flowing liquid and changes into a solid phase. The extruded dope 6 can be at a temperature low enough so that it is essentially non-flowing before entering the coagulation bath 10. However, the coagulation bath 10 does ensure or complete the coagulation of the filament, i.e., the conversion of the polymer from a dope solution 2 to a substantially solid polymer filament 12. The amount of solvent, i.e., polyphosphoric acid, removed during the coagulation step will depend on the residence time of the dope filament in the coagulation bath, the temperature of the bath 10, and the concentration of solvent therein.

Without desiring to be bound by any particular theory of operation, it is believed that the present invention is, in part, based on the discovery that long term fiber properties are better preserved if residual phosphorus levels are low. In part, this may be achieved by hydrolyzing PPA prior to its removal from the fiber in the belief that substantially hydrolyzed polyphosphoric acid may be effectively removed from the fiber to achieve low residual phosphorus. Typically, PPA is substantially hydrolyzed under conditions whereby the fiber remains substantially non-hydrolyzed. Although many modes of practicing the invention are recognizable to one skilled in the art when armed with the present invention, PPA may be conveniently hydrolyzed by heating the filament or yarn prior to washing and/or neutralization steps. One manner of hydrolysis includes convective heating of the coagulated fiber for a short period of time. As an alternative to convective heating, the hydrolysis may be effected by heating the wet, as coagulated filament or yarn in a boiling water or aqueous acid solution. The heat treatment provides PPA hydrolysis while adequately retaining the tensile strength of the product fiber. The heat treatment step may occur in a separate cabinet 14, or as an initial process sequence followed by one or more subsequent washing steps in an existing washing cabinet 14.

In some embodiments, the hydrolysis and removal are provided by (a) contacting the dope filament with a solution in bath or cabinet 14 thereby hydrolyzing PPA and then (b) contacting the filament with a neutralization solution in bath or cabinet 16 containing water and an effective amount of a base under conditions sufficient to neutralize sufficient quantities of the phosphoric acid, polyphosphoric acid, or any combination thereof in the filament.

After treatment to substantially hydrolyze polyphosphoric acid (PPA) associated with the coagulated filament, hydrolyzed PPA may be removed from the filament or yarn 12 by washing in one or more washing steps to remove most of the residual acid solvent/and or hydrolyzed PPA from the filament or yarn 12. The washing of the filament or yarn 12 may be carried out by treating the filament or yarn 12 with a base, or with multiple washings where the treatment of the filament or yarn with base is preceded and/or followed by washings with water. The filament or yarn may also be treated subsequently with an acid to reduce the level of cations in the polymer. This sequence of washings may be carried out in a continuous process by running the filament through a series of baths and/or through one or more washing cabinets. FIG. 1 depicts one washing bath or cabinet 14. Washing cabinets typically comprise an enclosed cabinet containing one or more rolls which the filament travels around a number of times, and across, prior to exiting the cabinet. As the filament or yarn 12 travels around the roll, it is sprayed with a washing fluid. The washing fluid is continuously collected in the bottom of the cabinet and drained therefrom.

The temperature of the washing fluid(s) impacts on the diffusion rates controlling the washing process, making the temperature selection a matter of practical importance. Preferably, temperatures between 20 and 90 C are used, depending on the residence time desired. The washing fluid may be applied in vapor form (steam), but is more conveniently provided in liquid form. Preferably, a number of washing baths or cabinets are used. The residence time of the filament or yarn 12 in any one washing bath or cabinet 14 will depend on the desired concentration of residual phosphorus in the filament or yarn 12, but preferably the residence time is in the range of from about 1 second to less than about two minutes. In a continuous process, the duration of the entire washing process in the preferred multiple washing bath(s) and/or cabinet(s) is preferably no greater than about 10 minutes, more preferably more than about 5 seconds and no greater than about 160 seconds.

In some embodiments, preferred bases for the removal of hydrolyzed PPA include NaOH; KOH; $Na_2CO_3$; $NaHCO_3$; $K_2CO_3$; $KHCO_3$; ammonia; or trialkylamines, preferably tributylamine; or mixtures thereof. In one embodiment, the base is water soluble. Typical aqueous bases include NaOH, KOH, $Na_2CO_3$, $NaHCO_3$, $K_2CO_3$, and $KHCO_3$ or mixtures thereof; more typically NaOH.

After treating the fiber with base, the process may optionally include the step of contacting the filament with a washing solution containing water or acid or both to remove all or substantially all excess base or base cations otherwise bound or associated with the polymer fiber. This washing solution can be applied in a washing bath or cabinet 18.

After washing, the fiber or yarn 12 may be dried in a dryer 20 to remove water and other liquids. The temperature in the dryer is typically 80° C. to 130° C. The dryer residence time is typically 5 seconds to perhaps as much as 5 minutes at lower temperatures. The dryer can be provided with a nitrogen or other non-reactive atmosphere. Then the fiber may be optionally further processed in, for instance, a heat setting device 22. Further processing may be done in a nitrogen purged tube furnace 22 for increasing tenacity and/or relieving the mechanical strain of the molecules in the filaments. Finally, the filament or yarn 12 is wound up into a package on a windup device 24. Rolls, pins, guides, and/or motorized devices 26 are suitably positioned to transport the filament or yarn through the process.

Shaped articles as described herein include extruded or blown shapes or films, molded articles, and the like. Films can be made by known techniques such as (1) casting the dope onto a flat surface, (2) extruding the dope through an extruder to form a film, or (3) extruding and blowing the dope film to form an extruded blown film. Typical techniques for dope film extrusion include processes similar to those used for fibers, where the solution passes through a spinneret or die into an air gap or fluid layer and subsequently into a coagulant bath. More details describing the extrusion and orientation of dope films can be found in Pierini et al. (U.S. Pat. No. 5,367,042); Chenevey, (U.S. Pat. No. 4,898,924); Harvey et al., (U.S. Pat. No. 4,939,235); and Harvey et al., (U.S. Pat. No. 4,963,428). Typically the dope film prepared is preferably no more than about 250 mils (6.35 mm) thick and more preferably it is at most about 100 mils (2.54 mm) thick.

Preferably, the phosphorus content of the dried filaments after removal of the hydrolyzed PPA is less than about 5,000 ppm (0.5%) by weight, and more preferably, less than about 4,000 ppm (0.4%) by weight, and most preferably less than about 2,000 ppm (0.2%) by weight.

The invention is further directed, in part, to a yarn comprising a plurality of the filaments of the present invention, fabrics that include filaments or yarns of the present invention, and articles that include fabrics of the present invention.

EXAMPLES

Experimental Test Methods

The test methods described below were used in the following Examples.

Temperature: All temperatures are measured in degrees Celsius (° C.).

Denier is determined according to ASTM D 1577 and is the linear density of a fiber as expressed as weight in grams of 9000 meters of fiber.

Tenacity is determined according to ASTM D 885 and is the maximum or breaking stress of a fiber as expressed as grams per denier.

Elemental Analysis: Elemental analysis of alkaline cation (M) and phosphorus (P) is determined according to the inductively coupled plasma (ICP) method as follows. A sample (1-2 grams), accurately weighed, is placed into a quartz vessel of a CEM Star 6 microwave system. Concentrated sulfuric acid (5 ml) is added and swirled to wet. A condenser is connected to the vessel and the sample is digested using the moderate char method. This method involves heating the sample to various temperatures up to 260° C. to char the organic material. Aliquots of nitric acid are automatically added by the instrument at various stages of the digestion. The clear, liquid final digestate is cooled to room temperature and diluted to 50 ml with deionized water. The solution may be analyzed on a Perkin Elmer optima inductively coupled plasma device using the manufacturers' recommended conditions and settings. A total of twenty-six different elements may be analyzed at several different wavelengths per sample. A 1/10 dilution may be required for certain elements such as sodium and phosphorus. Calibration standards are from 1 to 10 ppm.

Process Examples

Many of the following examples are given to illustrate various embodiments of the invention and should not be interpreted as limiting it in any way. All polymer solids concentrations, weight percents based on monomer, and polymer solution percent $P_2O_5$ concentrations are expressed on the basis of TD-complex as a 1:1 molar complex between TAP and DHTA. The TD-complex is believed to be a monohydrate.

In the following examples, poly([dihydroxy]para-phenylene pyridobisimidazole) filaments (also referred to herein as "PIPD", shown below in one of its tautomeric forms) were spun from a polymer solution consisting of 18 weight percent of PIPD in polyphosphoric acid. The solution was extruded from a spinneret, drawn across an air gap and coagulated in water. Wet bobbins not processed within 6 hours were refrigerated until further processed.

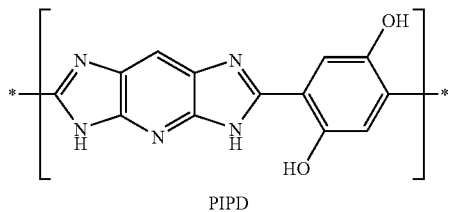

PIPD

Some of the following examples are illustrative of the difficulty in removing residual (poly)phosphoric acids from freshly spun fibers. For example, Example A shows typical levels of P in fibers when no purposeful removal in undertaken. Example B illustrates the difficulty of washing PPA from wet yarns using traditional washings with water. Example C illustrates the acid level believed to be a preferred higher acid concentration limit when treating PIPD fibers. At levels above this in certain embodiments, the fibers may begin to disintegrate.

Example D illustrates the difficulty of washing PPA from wet yarns using traditional washings with boiling water. Examples E-K show the benefits of carrying out a heat treatment step to hydrolyze residual polyphosphoric acids combined with washing of the fiber or yarn.

Example A

This example illustrates the difficulty of washing PPA from wet yarns using traditional washings with water. A solution of PIPD polymer and polyphosphoric acid having 81.6 wt % $P_2O_5$ was spun into fibers using a 250 hole spinneret. The wet as-coagulated yarn was allowed to air dry and was then analyzed for phosphorus. The sample was found to contain a very high level of phosphorus (63400 ppm) along with 175 ppm sodium.

A sample of the wet, as-coagulated PIPD yarn was then soaked in fresh water at room temperature for 5 minutes. The yarn sample was then rinsed for 20 seconds in fresh water, was allowed to air dry, and was then analyzed for phosphorus. The sample was found to contain 58500 ppm phosphorus and 453 ppm sodium.

A sample of the wet, as-coagulated PIPD yarn was then soaked for 5 minutes in gently boiling water at 100° C. This yarn sample was then rinsed for 20 seconds in fresh water at room temperature and then allowed to air dry. The sample was found to contain 55700 ppm phosphorus and 700 ppm sodium.

Example B

A solution of PIPD polymer and polyphosphoric acid having 82.5 wt $P_2O_5$ was spun into fibers using a 250 hole spinneret. The wet as-coagulated yarn was gently boiled in water at 100° C. for a period of 20 minutes. This yarn sample was then rinsed in fresh water for 10 seconds and allowed to air dry. The sample was found to contain 44500 ppm phosphorus and 1000 ppm sodium.

Example C

A solution of PIPD polymer and polyphosphoric acid having 81.9 wt % $P_2O_5$ was spun into fibers using a 250 hole spinneret. A sample of wet, as-coagulated PIPD yarn was treated in boiling 80% phosphoric acid (142° C.) for 15 seconds, washed in 91° C. water for 10 seconds, then in 60° C. baths of 2% aqueous caustic, water, 2% aqueous acetic acid, and water for 10 seconds each. The sample was then allowed to air dry. This sample was found to exhibit stuck or fused filaments and had a residual phosphorus level of 7.44%.

Another sample of this wet, as-coagulated PIPD yarn was placed in boiling (180° C.) 90% phosphoric acid. The sample rapidly disintegrated.

Example D

A solution of PIPD polymer and polyphosphoric acid having about 82.1 wt % $P_2O_5$ was spun into fibers using a 250 hole spinneret. Samples of the wet as-coagulated yarn were then boiled in water for a variety of times as shown in Table 1. The samples were then further washed at 60° C. in successive baths of water, 2 wt % aqueous caustic, water, 2% aqueous acetic acid, and then water for 20 seconds in each bath. After drying, the samples were found to contain the phosphorus content as shown in the table.

TABLE

| Sample | Time, min. | P (ug/g) | P (w %) |
|---|---|---|---|
| D-1 | 0 | 23800 | 2.38 |
| D-2 | 5 | 16200 | 1.62 |
| D-3 | 10 | 14000 | 1.4 |
| D-4 | 15 | 10700 | 1.07 |
| D-5 | 20 | 9180 | 0.918 |
| D-6 | 30 | 6380 | 0.638 |
| D-7 | 45 | 6320 | 0.632 |
| D-8 | 60 | 3920 | 0.392 |

Example E

A solution of PIPD polymer and polyphosphoric acid having 82.5 wt % $P_2O_5$ was spun into fibers using a 250 hole spinneret. Samples of wet, as-coagulated PIPD yarn were taken and first treated by high temperature, acidic hydrolysis conditions by employing boiling phosphoric acids of varying concentrations as shown in Table 2. Yarn samples were treated in hydrolyzing media for the times and temperatures shown. Washing of the samples was then done as shown in the Table 2. The washing steps included a combination of the steps of a) washing in water; b) washing in 2% aqueous sodium hydroxide in water; c) washing in water, d) washing in 2% aqueous acetic acid in water; and washing in water. The washings were performed for the indicated times and temperatures as shown in the table. It is possible to achieve residual phosphorus levels of under 2 weight % by such aggressive hydrolysis conditions when combined with washing.

TABLE 2

| Item | Media | Temp (° C.) | Time (s) | Water Temp/Time | Base Temp/Time | Water Temp/Time | Acid Temp/time | Water Temp/Time | P (wt %) | Na |
|---|---|---|---|---|---|---|---|---|---|---|
| 1-1 | 70% $H_3PO_4$ | 130 | 60 | 100/20 | —/— | —/— | —/— | 65/20 | 4 | 0.05 |
| 1-2 | 70% $H_3PO_4$ | 130 | 60 | 100/20 | 62/20 | —/— | —/— | 62/20 | 0.8 | 2.6 |
| 1-3 | 70% $H_3PO_4$ | 130 | 60 | 100/20 | 62/20 | 62/20 | 62/20 | 62/20 | 0.7 | 0.21 |
| 1-4 | 60% $H_3PO_4$ | 115 | 50 | 90/20 | 62/20 | —/— | —/— | 62/20 | 1.3 | 2.9 |
| 1-5 | 50% $H_3PO_4$ | 110 | 60 | 100/20 | —/— | —/— | —/— | 65/20 | 2.4 | 1.3 |
| 1-6 | 50% $H_3PO_4$ | 110 | 60 | 100/20 | 62/20 | —/— | —/— | 62/20 | 1.2 | 3.7 |
| 1-7 | 50% $H_3PO_4$ | 110 | 60 | 100/20 | 62/20 | 62/20 | 62/20 | 62/20 | 1.6 | 0.29 |
| 1-8 | 40% $H_3PO_4$ | 106 | 60 | 100/20 | 62/20 | —/— | —/— | 62/20 | 1.7 | 4.2 |
| 1-9 | 20% $H_3PO_4$ | 103 | 60 | 100/20 | —/— | —/— | —/— | 65/20 | 5.6 | 0.6 |
| 1-10 | 20% $H_3PO_4$ | 103 | 60 | 100/20 | 62/20 | —/— | —/— | 62/20 | 1.7 | 5.0 |
| 1-11 | 20% $H_3PO_4$ | 103 | 60 | 100/20 | 62/20 | 62/20 | 62/20 | 62/20 | 0.9 | 0.15 |
| 1-12 | — | — | — | —/— | —/— | —/— | —/— | —/— | 7.0 | 0.01 |
| 1-13 | Water | 100 | 60 | 100/20 | 62/20 | —/— | —/— | 62/20 | 2.8 | 4.7 |

Example F

A solution of PIPD polymer and polyphosphoric acid having 82.5 wt % $P_2O_5$ was spun into fibers using a 250 hole spinneret. A sample of wet, as-coagulated PIPD yarn was treated in atmospheric pressure steam (100° C.) for 60 seconds followed by rinsing in 60° C. water for 20 seconds. The sample was allowed to air dry and was found to contain 6.48 wt % P. Another similarly treated sample that was not air-dried was further washed at 60° C. in successive baths of 2 wt % aqueous sodium hydroxide, and then water for 20 seconds. After drying this sample was found to contain 2.1 wt % phosphorus.

Example G

A solution of PIPD polymer and polyphosphoric acid having 82.5 wt % $P_2O_5$ was spun into fibers using a 250 hole spinneret. A sample of wet, as-coagulated PIPD yarn so spun was treated in saturated steam at about 58 psig and 148° C. for 60 seconds followed by 20 second washes in the following baths at 60° C.: water, 2 wt % aqueous caustic, water, 2% aqueous acetic acid, and then water. After drying, the sample was found to contain 0.33 wt % phosphorus.

Another sample of wet, as-coagulated PIPD yarn was treated in saturated steam at 100 psig and 165° C. for 60 seconds followed by the same washing steps as before. The washed and dried sample was found to contain 0.11 wt % phosphorus.

Examples H and I show the use of dry heat to carry out the rapid hydrolysis. Example J demonstrates the use of steam heat to carry out the hydrolysis.

Example H

A solution of PIPD polymer and polyphosphoric acid having 82.1 wt % $P_2O_5$ was spun into fibers using a 100 hole spinneret. The wet, as-coagulated PIPD yarns were strung up to pass through a one-foot long nitrogen-purged tube oven. Table 3 shows the influence of tube oven temperature and residence time on the resulting levels of phosphorus in the samples following washing and drying. All samples were washed for 20 seconds each in 60° C. baths of water, followed by 2% aqueous sodium hydroxide, water, 2% acetic acid in water, and water. Phosphorus levels under 1 w % are obtained under many conditions using dry heat hydrolysis of wet, as coagulated yarn followed by the indicated washings.

TABLE 3

| Item | Oven Temp (C.) | Residence Time (s) | Yarn dpf | P (micrograms/gram) | Na (micrograms/gram) |
|---|---|---|---|---|---|
| H-1 | 180 | 30 | 1.5 | 6690 | 807 |
| H-2 | 180 | 20 | 2 | 7880 | 643 |
| H-3 | 180 | 30 | 2 | 7370 | 384 |
| H-4 | 180 | 20 | 2 | 8800 | 439 |
| H-5 | 180 | 10 | 2 | 23600 | 698 |
| H-6 | 200 | 10 | 2 | 15600 | 503 |
| H-7 | 200 | 20 | 2 | 3210 | 605 |
| H-8 | 200 | 30 | 2 | 3650 | 454 |
| H-9 | 200 | 30 | 1.5 | 3510 | 525 |
| H-10 | 220 | 30 | 1.5 | 3310 | 484 |
| H-11 | 220 | 30 | 2 | 2450 | 524 |
| H-12 | 220 | 20 | 2 | 2310 | 395 |
| H-13 | 220 | 10 | 2 | 12500 | 374 |
| H-14 | 240 | 10 | 2 | 2910 | 294 |
| H-15 | 240 | 20 | 2 | 2500 | 210 | dpf is denier per filament

Example I

A solution of PIPD polymer and polyphosphoric acid having 82.7 wt % $P_2O_5$ was spun into fibers using a 250 hole spinneret. As described in Example H, a wet, as coagulated PIPD yarn was treated continuously in an oven, however, the residence times and the temperatures were as shown in Table 4. This time the yarn samples were only treated for 20 seconds in each of the following baths at 45-50° C., water, 2% aqueous sodium hydroxide, and water. Residual phosphorus and sodium values are given in Table 3 and illustrate the benefits of the high temperature hydrolysis treatment on reducing the level of residual phosphorus.

TABLE 4

| Item | Oven Temp (° C.) | Residence Time (s) | P (micrograms/gram) | Na (micrograms/gram) |
|---|---|---|---|---|
| I-1 | 140 | 30 | 21600 | 25600 |
| I-2 | 160 | 30 | 16600 | 27300 |
| I-3 | 180 | 30 | 11000 | 20900 |
| I-4 | 200 | 30 | 5720 | 24200 |
| I-5 | 220 | 30 | 3110 | 20500 |
| I-6 | 240 | 30 | 3140 | 24500 |
| I-7 | — | — | 21200 | 39700 |
| I-8 | — | — | 21900 | 40000 |

To establish phosphorus levels in fiber before treatment, the wet, as-quenched yarn as used above was analyzed for phosphorus and was found to contain 34600 ppm. After drying this sample was found to contain 63900 ppm phosphorus. The difference in the percent weight of phosphorus between the yarn samples was due to the extra liquid in the wet yarn.

Example J

A solution of PIPD polymer and polyphosphoric acid having 82.1 wt $P_2O_5$ was spun into fibers using a 100 hole spinneret. Wet, as-coagulated PIPD yarn was strung up to pass through a one-foot long tube oven purged with atmospheric pressure steam. Table 5 shows the influence of temperature and residence time on the resulting levels of phosphorus in the samples following washing and drying. All samples were washed for 20 seconds each in 60 C baths of water, followed by 2% aqueous sodium hydroxide, water, 2% aqueous acetic acid, and water. Phosphorus levels under 1 wt % are again easily obtained under preferred conditions.

TABLE 5

| Item | Oven Temp (C.) | Residence Time (s) | P (micrograms/gram) | Na (micrograms/gram) |
|---|---|---|---|---|
| J-1 | 280 | 41 | 2500 | 697 |
| J-2 | 250 | 41 | 6910 | 890 |
| J-3 | 230 | 41 | 6550 | 833 |
| J-4 | 230 | 30 | 3910 | 776 |
| J-5 | 230 | 20 | 3490 | 714 |
| J-6 | 230 | 10 | 22400 | 793 |
| J-7 | 200 | 10 | 24800 | 928 |
| J-8 | 200 | 20 | 3870 | 819 |
| J-9 | 200 | 30 | 6040 | 1180 |
| J-10 | 180 | 30 | 7440 | 613 |
| J-11 | 180 | 20 | 9880 | 391 |

Example K

PIPD filaments were spun from a polymer solution consisting of 18 weight percent of PIPD in polyphosphoric acid (82.1 wt % $P_2O_5$). The solution was extruded from a spinneret having approximately 250 holes, drawn across an air gap and coagulated in water. The wet yarns were processed at 61 meters/min (200 ft/min) on the pair of heated rolls operating at measured surface temperatures of 201-221° C. and wound up on bobbins. The yarns that had been processed on hot rolls were observed to be very stiff and have excessive fusing of individual filaments. In addition, undesirable fiber residue was observed on the hot rolls. Additional processing details and results are shown in Table 6. The yarns on the bobbins were then washed and neutralized by immersing the bobbins for five minutes each in five consecutive baths that were at room temperature. The baths were, in order, water; 2% sodium hydroxide in water; water; 2% acetic acid in water; and water. The yarns on the bobbins were then allowed to air-dry and a sample of yarn was taken and the residual phosphorus content was found to be very variable, ranging from about 0.77 weight percent to about 3.42 weight percent phosphorus.

TABLE 6

| Item | Roll Temp ° C. | Tension | Yarn Denier | Phosphorus (wt %) |
|------|----------------|---------|-------------|-------------------|
| K-1  | 202            | 250     | 503         | 3.42              |
| K-2  | 201            | 250     | 465         | 1.77              |
| K-3  | 221            | 250     | 458         | 0.77              |

The disclosure of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A process for removing phosphorus from a yarn spun from a polymer solution containing polyphosphoric acid, the yarn comprising at least about 1.5 percent by weight of the yarn of phosphorus, comprising contacting the yarn with a base and washing the yarn with an aqueous fluid, wherein the yarn is provided by heating a spun multifilament yarn comprising the polymer and polyphosphoric acid to at least 120 degrees Celsius for a time effective to hydrolyze polyphosphoric acid.

2. The process of claim 1 wherein the phosphorus content of the yarn prior to contacting the yarn with the base is in the range of from 2 to 20 percent based on yarn weight.

3. The process of claim 1 wherein the phosphorus content of the yarn prior to contacting the yarn with the base is 4 to 15 percent based on yarn weight.

4. The process of claim 1 wherein contacting the yarn with the base includes spraying, coating, flowing, drawing, dipping, or any combination thereof.

5. The process of claim 4 wherein the base includes sodium hydroxide, potassium hydroxide, ammonium hydroxide, sodium bicarbonate, or any combination thereof.

6. The process of claim 1 wherein the aqueous fluid contains an acid.

7. The process of claim 6 wherein the acid is a volatile acid.

8. The process of claim 7, wherein the volatile acid includes acetic acid or propionic acid, or any combination thereof.

9. The process of claim 1 wherein the polymer comprises a polyareneazole.

10. The process of claim 9 wherein the polyareneazole is a polypyridazole.

11. The process of claim 10 wherein the polypyridazole is a polypyridobisimidazole.

12. The process of claim 11 wherein the polypyridobisimidazole is poly(1,4-(2,5-dihydroxy)phenylene-2,6-pyrido[2,3-d:5,6-d']bisimidazole.

13. The process of claim 9 wherein the polyareneazole is a polybenzobisoxazole.

14. The process of claim 1, wherein the yarn contains less than 0.1 percent phosphorus based on yarn weight after washing with the aqueous fluid.

15. The process of claim 1, wherein the base is aqueous sodium hydroxide or the aqueous fluid contains acetic acid, or both.

16. The process of claim 1, wherein the duration of the contacting step is no more than 30 seconds.

17. The process of claim 1, wherein the duration of the washing step is no more than 30 seconds.

18. The process of claim 1, wherein the step of contacting the yarn with a base begins before the step of washing the yarn with an aqueous fluid.

19. The process of claim 1, wherein the time effective to hydrolyze polyphosphoric acid is up to about 120 seconds.

* * * * *